(12) United States Patent
Hirsch et al.

(10) Patent No.: US 7,823,690 B2
(45) Date of Patent: Nov. 2, 2010

(54) MULTI-LAYERED, PEELABLE HYGIENIC COVER FOR A STETHOSCOPE

(76) Inventors: Bruce Hirsch, 3 Driftwood Dr., Port Washington, NY (US) 11050; David Miller, 114 Middlesex Rd., Buffalo, NY (US) 14216-3522

( * ) Notice: Subject to any disclaimer, the term of this patent is extended or adjusted under 35 U.S.C. 154(b) by 6 days.

(21) Appl. No.: 12/215,197

(22) Filed: Jun. 25, 2008

(65) Prior Publication Data
US 2009/0014232 A1    Jan. 15, 2009

Related U.S. Application Data

(60) Provisional application No. 60/937,106, filed on Jun. 25, 2007.

(51) Int. Cl.
*A61B 7/02* (2006.01)
(52) U.S. Cl. ................................ 181/131; 600/528
(58) Field of Classification Search ............... 181/131; 600/528; 381/67; D24/134
See application file for complete search history.

(56) References Cited

U.S. PATENT DOCUMENTS

| 2,650,269 | A | * | 8/1953 | Webb | 379/452 |
| 3,130,810 | A | * | 4/1964 | Werner | 181/135 |
| 3,213,960 | A | * | 10/1965 | Wagner | 181/126 |
| 3,255,841 | A | * | 6/1966 | Hasbrouck | 181/126 |
| 5,363,843 | A | * | 11/1994 | Daneshvar | 128/897 |
| 5,428,193 | A | * | 6/1995 | Mandiberg | 181/131 |
| 5,448,025 | A | * | 9/1995 | Stark et al. | 181/131 |
| 5,466,898 | A | * | 11/1995 | Gilbert et al. | 181/131 |
| 5,486,659 | A | * | 1/1996 | Rosenbush | 181/131 |
| 5,528,004 | A | * | 6/1996 | Wurzburger | 181/131 |
| 5,564,431 | A | * | 10/1996 | Seward | 600/528 |
| 5,587,561 | A | * | 12/1996 | Budayr et al. | 181/131 |
| 5,686,706 | A | * | 11/1997 | Wurzburger | 181/131 |
| 5,747,751 | A | * | 5/1998 | Weckerle et al. | 181/131 |
| 5,808,244 | A | * | 9/1998 | Knight et al. | 181/131 |
| 5,813,992 | A | * | 9/1998 | Henwood | 600/528 |
| 5,921,941 | A | * | 7/1999 | Longobardo et al. | 600/528 |
| 5,949,032 | A | * | 9/1999 | Wurzburger | 181/131 |
| 6,009,971 | A | * | 1/2000 | Weidman et al. | 181/131 |
| 6,019,187 | A | * | 2/2000 | Appavu | 181/131 |
| 6,064,735 | A | * | 5/2000 | Wilkes | 379/452 |
| 6,186,957 | B1 | * | 2/2001 | Milam | 600/528 |
| 6,206,134 | B1 | * | 3/2001 | Stark et al. | 181/131 |
| 6,467,568 | B1 | * | 10/2002 | Kemper | 181/131 |
| 6,510,918 | B2 | * | 1/2003 | Bates | 181/131 |
| 6,520,281 | B1 | * | 2/2003 | Deslauriers et al. | 181/131 |
| 6,575,917 | B2 | * | 6/2003 | Giroux et al. | 600/528 |
| 2005/0257996 | A1 | * | 11/2005 | Brown et al. | 181/131 |
| 2006/0076184 | A1 | * | 4/2006 | Robinson | 181/131 |
| 2007/0074929 | A1 | * | 4/2007 | Garcia et al. | 181/131 |

* cited by examiner

*Primary Examiner*—Jeffrey Donels
*Assistant Examiner*—Jeremy Luks
(74) *Attorney, Agent, or Firm*—Thomas A. O'Rourke; Bodner & O'Rourke, LLP (57) ABSTRACT

A disposable stethoscope cover that covers at least the surface of the diaphragm is disclosed. The cover contacts a patient during use and reduces transmittal of microorganisms. The cover is in the form of a flexible sheet having a top and a bottom surface. The sheet has an adhesive material on a portion of the surface thereof that secures the sheet to the surface of the diaphragm. The sheet further includes at least one wing extending from the sheet. The wing has an adhesive on at least one surface thereof for securing the wing to the sheet when the wing is folded over at least a portion of a tube section of the stethoscope.

32 Claims, 7 Drawing Sheets

MULTI-LAYERED, PEELABLE HYGIENIC COVER FOR A STETHOSCOPE

This application claims priority on U.S. Provisional Application Ser. No. 60/937,106 filed on Jun. 25, 2007 the disclosures of which are incorporated herein by reference.

FIELD OF INVENTION

This invention relates to medical equipment and accessories, and particularly to multi-layered, disposable sanitary covers for a physician's stethoscope.

BACKGROUND OF INVENTION

A stethoscope is an acoustic device used largely, though not exclusively, by medical practitioners to listen to internal sounds of the human body, thus aiding in the diagnosis of certain diseases and conditions. It is most commonly used to hear sounds generated by the heart and lungs, but is sometimes used to listen to the stomach and intestines, blood flowing in arteries and veins, and also to developing fetuses in pregnant women.

A binaural stethoscope consists of a chest piece connected to Y-shaped flexible tubing which terminates into two ear pieces. The chest piece is placed on the region of the body requiring auscultation by the physician.

The chest piece often is composed of a diaphragm that vibrates as a result of body sounds, creating acoustic pressure waves, which are conducted through the air-filled tubing to the ear pieces where they are received and interpreted by the practitioner. Some stethoscopes have a chest piece that is two-sided, with a diaphragm on one side, and a bell or hollow cup shape on the opposite side. The diaphragm is better adapted for transmission of higher frequency sounds, while the bell is better adapted for low frequency transmissions.

Electronic stethoscopes, with a transducer and amplifier in the chestpiece are available as well, and these are used in the same manner as traditional stethoscopes, with the chestpiece placed directly on the skin of the patient, or occasionally on the patient's clothing.

A serious concern among medical practitioners is the occurrence, within 48 hours of admittance to a hospital or within 30 days of discharge, of an infection secondary to the patient's original condition. Nosocomial (hospital-acquired) infections, such as *Staphylococcus aureus* (including Methicillin-resistant *Staphylococcus aureus* [MRSA]), *Pseudomonas aeruginosa*, *Clostridium difficile*, and *Acinetobacter baumanni*, are estimated to affect one hospital patient in ten, contribute to the death of many of those patients, prolong hospitalization and increase health care costs. It is also estimated that one-third of all nosocomial infections may be prevented.

There are numerous vehicles for the spread of microorganisms, including airborne propagation, transmission through sources of food and water, and of course, physical transmission through direct surface-to-body contact, particularly during care-giving activities. Transmission can be significantly reduced by the use of physical barriers to transmission, such as gloves, equipment coverings, and drapes. Removal of disease-causing materials through handwashing and cleaning of equipment is also highly effective in reducing infection transmission.

Disposable gloves greatly increase the safety of interactions during patient contacts, by providing a clean surface for each patient. Similar contact occurs when doctors, nurses, and other health care providers utilize a stethoscope and moves from patient to patient to accomplish physical examinations, monitor patients' blood pressure, or during clinical emergencies.

Studies have shown that a stethoscope's diaphragm and bell can harbor pathogenic agents, leading many medical personnel to routinely swab those areas with isopropyl alcohol between patient contacts. Despite its necessity, this routine is understandably inconvenient and has precipitated development of sanitary stethoscope covers, so that the instrument can be covered with a disposable cover Stethoscope covers have been designed to protect soiling of the stethoscope, provide decoration, and enhance comfort to the patient.

A number of inventions have attempted to create highly functional hygienic stethoscope covers, but all have fallen short of providing the caregiver with the high level of convenience and ease of use desired, while maintaining the instrument's sound transmission capability.

DESCRIPTION OF THE PRIOR ART

One series of patents describe a plastic cover to snap over the diaphragm of the chestpiece, and appears in U.S. Pat. No. 6,019,187. Similar embodiments are presented in U.S. Pat. Nos. 4,867,268; 4,461,368. This design seeks to provide a durable hard cover which could be disposed of, or alternately be cleaned for reuse. A similar patent, U.S. Pat. No. 3,255,841, covers the bell in a similar manner. In a practical sense, a non-renewable cover provides little gain in convenience for the physician, as the required cleaning of the diaphragm or bell itself was replaced by cleaning of the cover, although it can potentially be deferred to a later time. The cover does also serve as a thermal insulator for the metallic chest piece, which normally requires warming by a caregiver's hands prior to placement on the patient's skin. Many stethoscope models now feature non-chill rims, reducing or eliminating the need for this characteristic.

Another modest gain of those patents is that the sturdy hard plastic cover could be applied to a stethoscope to create a hygienically clean surface for immediate use, after a caregiver had once utilized the instrument but was suddenly faced with an urgent medical situation where the requisite time for a thorough cleaning was lacking. However, to accommodate replacement after each ordinary use or after the aforementioned urgent situation, a new bulky plastic cover would need to be retrieved from a supply station, or would need to have been transported around in the care-givers pocket in a sanitary container. Neither option maximizes the convenience that is essential to assure regular use to prevent nosocomial transmission of infectious pathogens.

Flexible covers for the diaphragm, such as U.S. Pat. No. 5,921,941, have similar drawbacks to rigid covers. They are relatively bulky, and therefore carrying a large number of these is impractical. Reusable covers impregnated with antimicrobial agents do not provide adequate protection as a disposable covers, due to the inability of antimicrobial agents to inactivate all types of pathogens, and the time required for antimicrobials to work.

Sleeve type covers describe a flexible covering with varying configurations, but all are similar in nature to a condom. Several such designs are shown in U.S. Pat. Nos. 738,960; 5,564,431; 5,747,751; 4,871,046, and 5,365,023. These designs are not as bulky as the hard plastic covers, but are still limited by the need to either carry many units, or to resupply from a supply station. While the condom-type coverings do provide comprehensive protection, application and removal are relatively difficult and time consuming, making these less than ideal solutions. Furthermore, because of the nature of their application to the chest piece, this series of patents as well as the diaphragm covers degrade sound transmission. A contiguous body or connected solid bodies are more conducive to sound transmission than an air-filled void, or other damping material which is why a physician generally prefers to place the chest piece directly on the patient's skin rather than atop clothing or a hospital gown. Air gaps reduce the sound transmission capability of the stethoscope system, and must be avoided for maximum diagnostic performance.

Both the acoustic degradation and the logistical drawback of prior designs were largely addressed in a third series of patents. U.S. Pat. Nos. 5,587,561, 5,686,706, and 5,949,032 disclose a flexible cover consisting of multiple layers, such that an exposed layer could be peeled away and discarded. The logistical limitation of prior arrangements is thus solved. Also, this series of patents suggest the use of adhesive to attach the stack of layers to the diaphragm. This would tend to eliminate the sound transmission problems of earlier inventions, except on one of the proposed embodiments that advocated a non-homogenous layer of adhesive, which would produce degradation similar to that of trapped air pockets. However, while generally solving the drawbacks of the prior art, several new problems are created.

First, the designs prescribe planar disc-shaped layers that approximate the diameter of the chestpiece. Such an arrangement is noticeably flawed as a physician's exam typically includes sliding the chest piece across a patient's bare body surface in order to perform auscultation of several different regions. The edges of the chestpiece and cover will no doubt make contact with a patient's skin, body hair, clothes and bedding rendering the chestpiece edge periphery susceptible to loading with pathogenic material. It is only a partial solution to have a flange as suggested by the alternate embodiment of U.S. Pat. No. 5,587,561 without more positive assurance that patient to patient transfer of pathogens is not occurring from the periphery of the stethoscope chestpiece or the periphery of the cover.

A second flaw relates to the practicality of removal of exposed layers in a multi-level stack. Although U.S. Pat. No. 5,686,706 does depict a pull tab, a caregiver would nonetheless be inconvenienced by attempting to separate and peel away one thin, onion-skin-like layer from the stack while moving briskly between patient contacts. It would likely result in a care-giver roughly thumb-nailing the tab and likely grabbing several sheets while expeditiously seeking to dispose of a contaminated layer. Wearing gloves would complicate this procedure. Both of these new problems found in the multi-layered protective covers of the third series of patents, are solved by the current invention.

BRIEF SUMMARY OF THE INVENTION

The present invention provides a flexible protective sheet over a stethoscope as well as a means of affixing the flexible protective covering to the stethoscope. The covering not only provides a barrier to contact with the chestpiece, diaphragm and bell, it also prevents contact with the tubing which connects to the stethoscope's chest piece as well. The invention additionally provides a simple, easy to use means of peeling away one or more of a plurality of these thin covering layers that are stacked on a stethoscope. In this manner, an exposed covering, which may be contaminated by contact with a patient's body, can be removed and a fresh clean surface can be used for the next patient. Easy removal of an individual layer is achieved with this invention by providing a large tabbed region on each sheet, which is treated in such a way as to not adhere to the other layers of the stack. This tab can be easily grasped by the caregiver, even with gloved hands.

In one embodiment, the layers are to be cut in such a way that each successive layer is slightly larger than the layer below, preventing contact between the patient's skin and the edges of layers below the top sheet.

DETAILED DESCRIPTION OF THE PREFERRED EMBODIMENTS

The present invention is directed to a flexible sheet to be used as a protective cover for a stethoscope. In a preferred embodiment there are a plurality of sheets that are removably secured together by a suitable means such as adhesive or electrostatic cling etc., which may be secured to a base layer. It is preferred that the protective layers are releaseably attached to the adjacent layer each other so that the outermost layer may be readily removed and discarded after use leaving a new sheet on the outer surface. The sheet is preferably a single layer of a flexible material, preferably a thin thermoplastic film, such as ethylene vinyl alcohol copolymer (EVOH), polyvinyl alcohol (PVOH), low-density polyethylene (LDPE), linear low-density polyethylene (LLDPE), high density polyethylene (HDPF), polypropylene, etc. The sheets could also be made from any suitable thin film such as a paper based material or a multilayer material as well. If a base layer is used, the base layer could be made from the same material, but preferably of greater thickness, or alternatively made of some other more substantial backing material. The protective layers would ideally be treated so as to be anti-microbial.

Figure 4:
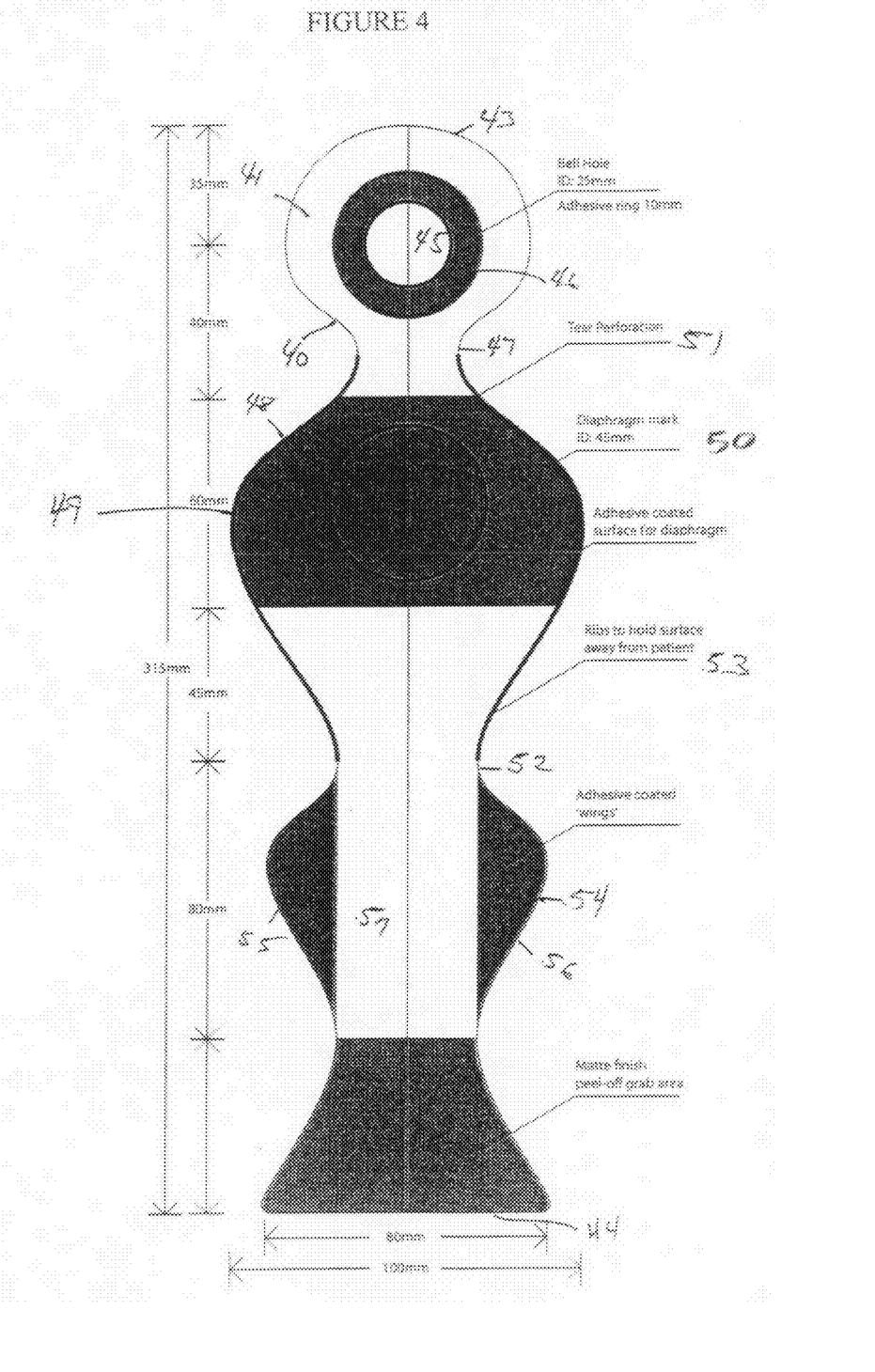
FIG. 4 shows another embodiment of the cover of the present invention.

One preferred embodiment is shown in FIG. 4. There is a flexible sheet 40 that has a top surface 41 and a bottom surface 42. If a thicker sheet is desired there can be sidewalls on the sheet extending from the top surface to the bottom surface.

For ease of understanding the invention the sheet has a head or top end 43 and a bottom end 44. Top end 43 preferably has an orifice 45 extending from the top surface to the bottom surface of the sheet. The orifice 45 is a bell hole through which the tubing of the stethoscope may pass. One end of the tubing splits to form a pair of and the pair of ends are placed in a user's ears. The other end of the tubing has the bell or diaphragm connected there to. The sheet of the present invention rest on the end of the bell or diaphragm that is secure to the tubing. An adhesive 46 or other suitable security means may be present on one surface of the top end of the sheet to secure the sheet. In a preferred embodiment the adhesive or other securing means is a ring positioned around the opening 45.

The sheet of the present invention may have any shape or length. It has been found however, that the shape shown in FIG. 4 has particular advantages. Extending from the head 43 there is a neck 47. The neck 47 preferably has a cross section less than the cross section of the head 43 on the shoulders 48. Adjacent to the shoulders 48 is the breast 49. At least one side of the breast and shoulder 48 have an adhesive on at least a portion of this area. In a preferred embodiment the adhesive is over the entire surface of the breast and shoulder as depicted in the drawing. If desired a greater or smaller area can be provided with the adhesive. In about the center of the breast and shoulder region there may be a guide 50 that shows where the diaphragm of the stethoscope can be positioned so that the sheet does not interfere with sound passing through the diaphragm. The adhesive in the shoulder/breast region secures the top sheet to the diaphragm of the stethoscope. The adhesive on the guide 50 secures the sheet to the surface of the stethoscope that contacts the patient. The remainder of the adhesive on the breast/shoulder area can secure the sheet to other areas of the diaphragm such as the sidewall. It is preferred that there be a tear perforation 51 where the shoulder 48 meets the neck 47 This perforation permits a used sheet to be removed from the stack of sheets.

The sheet has a narrowing portion or waist 52 extending from the wider breast region. In one embodiment there can be a raised rib 53 on an outer edge of the sheet. This rib holds the surface of the sheet away from the patient. The rib 53 preferably extends along the perimeter from the waist 52 to the neck 47 and is preferably on each edge. The rib may be formed from a bead of a plastic material or it may be integral with sheet when the sheet is formed such as by extrusion to secure that portion of the sheet thereto.

Extending from the waist 52 are hips 54. The hips 54 preferably have first and second wings 55 and 56 and a body portion 57. These wings preferably have an adhesive on one surface thereof. The wings may be folded over the tubular portion of the stethoscope. The body area is preferably without adhesive but could have an adhesive if desired.

The adhesive is preferably of the type used by "Post It" type notes and the like, although any suitable adhesive can be used. In place of an adhesive an electrostatic charge can be used.

At the base 44 of the sheet there is a peel off or grab area that permits a user to grab the end of the sheet and remove it from the stethoscope. These areas may be provided with an anti cling material to facilitate separation of the sheets from the adjacent sheet. During removal the sheet would typically separate at the tear perforation between the neck and the shoulder if a tear perforation is present. In a preferred embodiment there is a stack of individual sheets similar to the sheets shown in FIG. 4. The stack of sheets has the individual sheets secured together by the adhesive that is on at least one surface of the sheet. The sheets are shown in FIG. 4 to have a particular shape or configuration. One skilled in the art will recognize that the sheets can be of other shapes as well.

Figure 5:
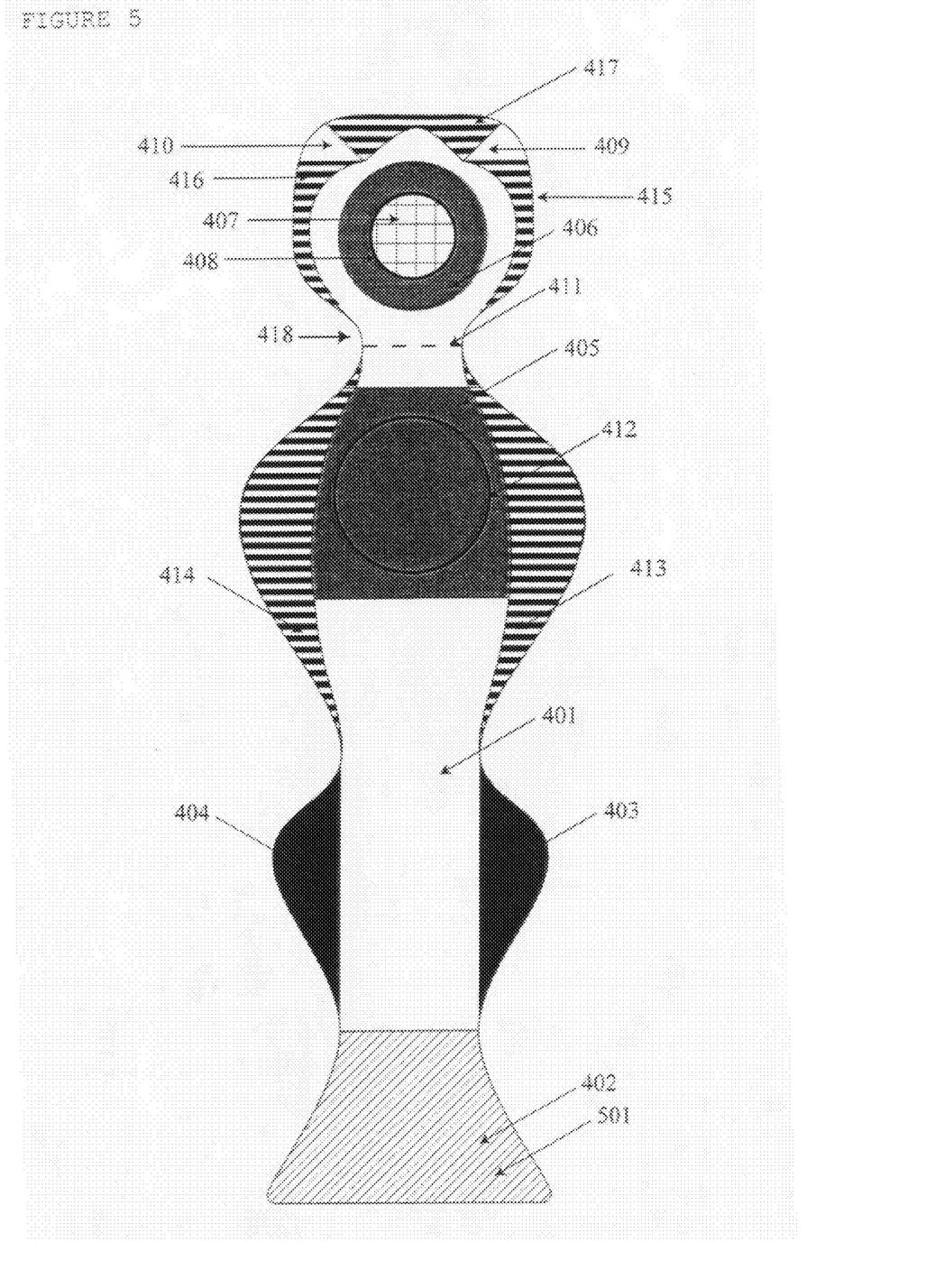
FIG. 5 shows a preferred embodiment of the stethoscope cover in the flat, unassembled configuration. The bottom side sheet is shown, with adhesive appliqués and contoured regions denoted.
Figure 6:
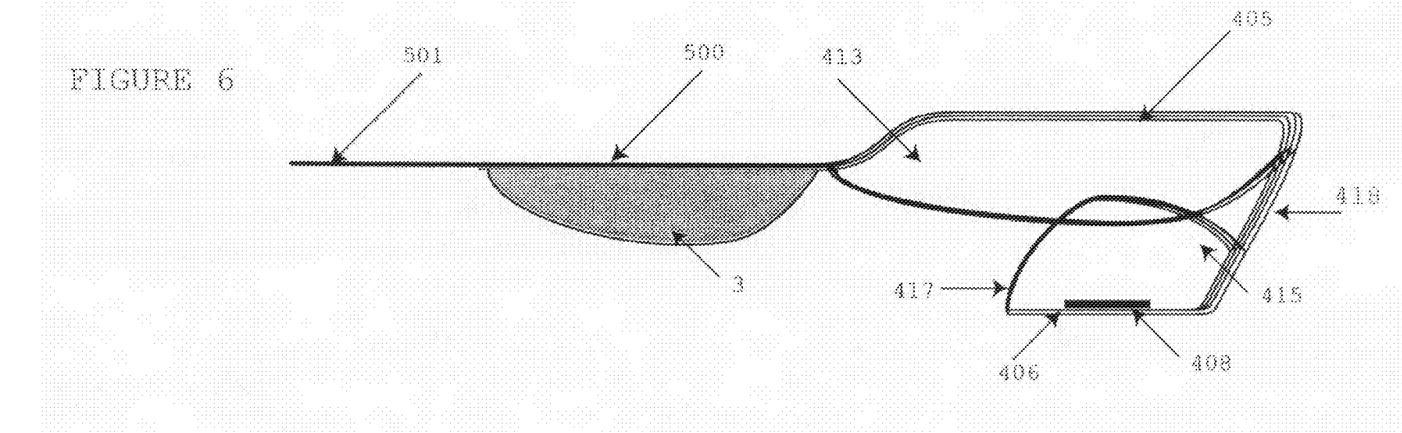
FIG. 6 shows a side view of the base layer of the invention, with the diaphragm and bell covers in their molded shape.
Figure 6A:
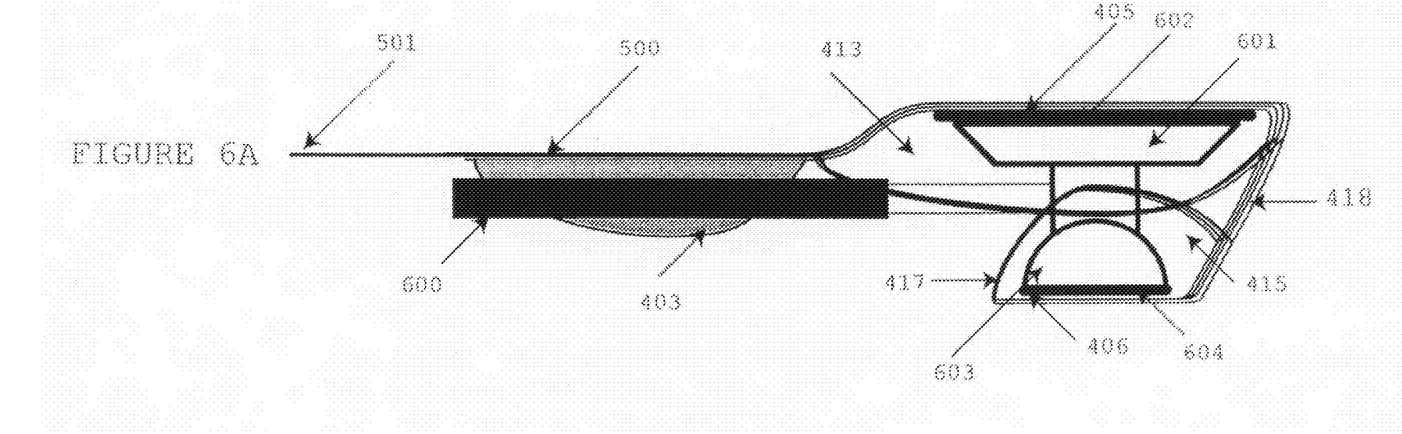
FIG. 6A shows the invention in the same configuration as FIG. 6, with a stethoscope head and tube.
Figure 7:
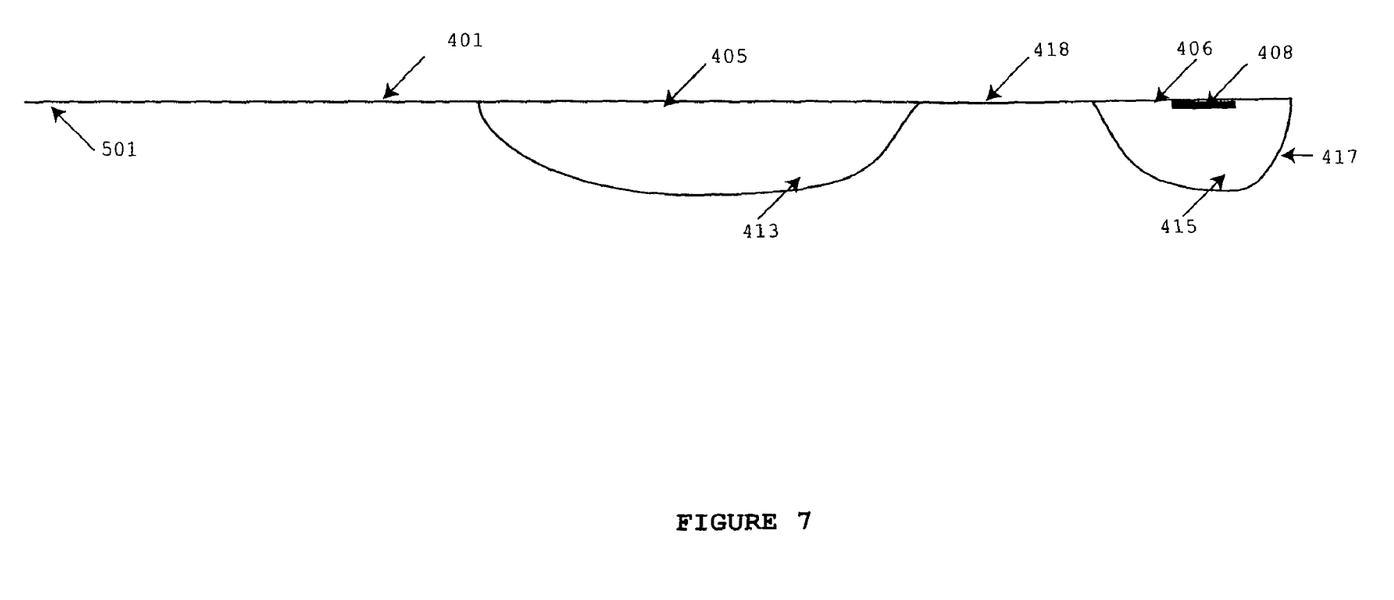
FIG. 7 shows the stethoscope cover with the diaphragm covering wings and bell cover in position for use.

Turning to FIGS. 5 to 7, the panels 403 and 404 serve to wrap around the stethoscope tubing or wiring, and are preferably coated with a low-tack contact adhesive that will stick to a like surface, allowing for the panels to hold the stethoscope cover around the tubing, yet allow for easy removal.

One embodiment of the invention is shown in FIG. 5 as it would be packaged in a flat configuration. The base layer 401 would be manufactured of a thin flexible material, coated with an adhesive in regions 403, 404, 405 and 406. The tabs 403 and 404 are used to secure the stethoscope cover to the stethoscope tubing 600, and the adhesive regions 405 and 406 will attach the cover to the diaphragm and bell respectively. In about the center of the breast and shoulder region there may be a guide 412 that shows where the diaphragm of the stethoscope can be positioned so that the sheet does not interfere with sound passing through the diaphragm.

In one embodiment, the panels 413, 414, 415, 416, and 417 are to be formed in such a way that they will curve around the contours of the stethoscope head when applied, shown in FIG. 6A. The stethoscope has tubing 600 that extends from the diaphragm. The diaphragm has a middle portion 601 which supports the stethoscope chestpiece/diaphragm housing as well as the diaphragm surface 602. The middle portion 601 of the stethoscope housing separates the bell housing 603 from the diaphragm surface. On the bell housing 603 is the bell surface ring 604.

The panels 409 and 410 will facilitate covering of the bell when applied, and will stretch so as to allow for the product to be packed in a flattened configuration. The perforations 411 will allow for the removal of the bell cover, for use with stethoscopes which are equipped only with a diaphragm or a single transducer. This arrangement allows for the diaphragm to nest in the cover, preventing contact between the patient and the stethoscope head.

The bell cover will be fitted with a hole 407, and an embossed ring 408, to allow for the passage of sound, while preventing contamination of the bell.

The pull tab 501 is to be treated in such a manner as to be anti-cling with other layers 500, or be manufactured in such a way that it is easy to separate the top layer from the remaining sheets. Item 402 is the similar region of the base layer, which is also to be treated in such a way as to ease removal of the sheet above.

The backing layer would ideally be covered with ten (10) to twenty (20) sheets of material 500, allowing caregivers to service a number of patients before applying a new unit to the stethoscope. In one embodiment, each successive layer would be slightly smaller than the previous layer, so as to eliminate the possibility of contact between the patient and any layer besides the top layer of the sheets 500.

Figure 1:
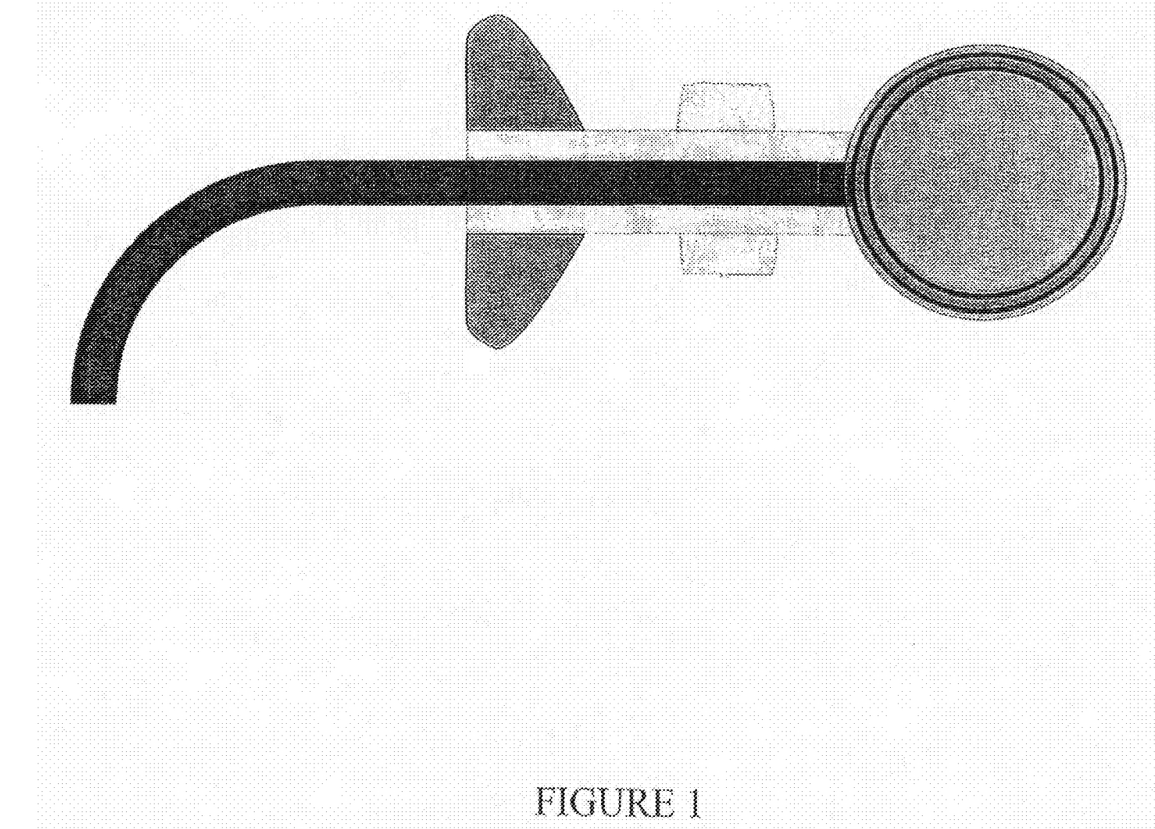
FIG. 1 shows one embodiment of the present invention where there is a typical stethoscope diaphragm connected to a rubber tube, with the invention attached via adhesive, or other means, to the diaphragm, and via tabs wrapped around the rubber hose.
Figure 2:
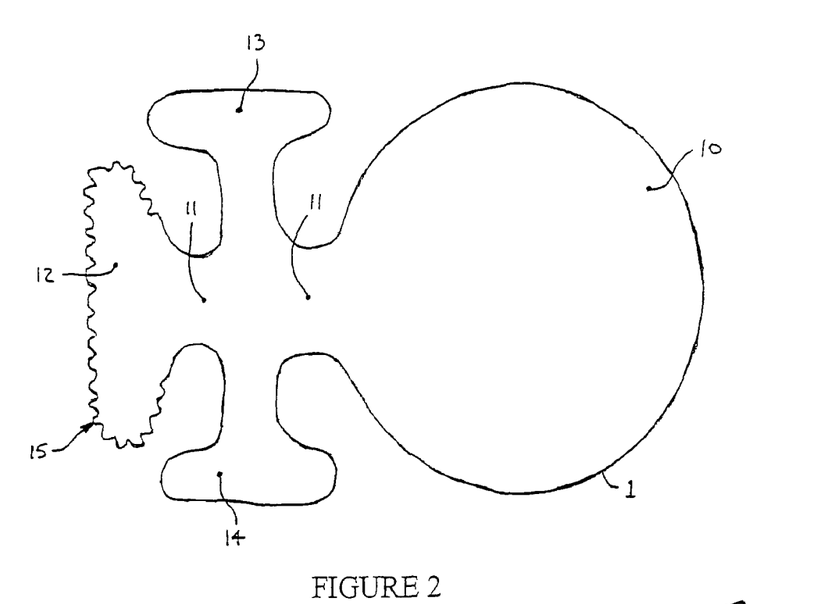
FIG. 2 shows the base layer of the cover, but in the flattened, unassembled condition.
Figure 2A:
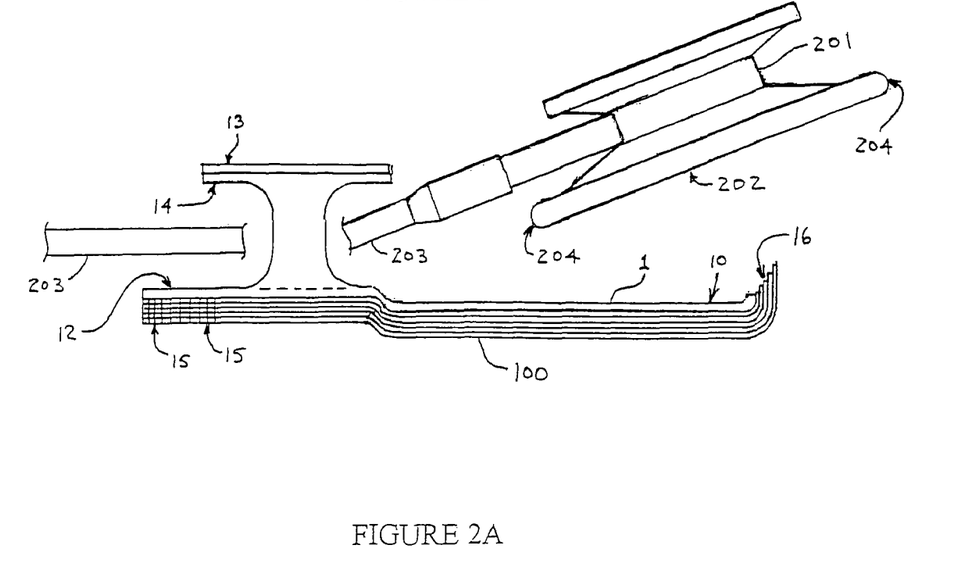
FIG. 2A shows a side view of the protective cover of FIG. 1 with the tabs wrapped about the rubber hose of the stethoscope and attached to each other via adhesive, with the diaphragm of the stethoscope not yet pressed into the disk portion of the protective cover.

Another embodiment of the invention is shown in FIG. 2 as it would be retrieved, for example, from a dispenser. The base layer 1 of the cover is in the form of, for example, a disk shape 10 that has a tab such as rectangular tab 11 that terminates in, for example, a widened fish-tail shaped area 12 constituting a "pull tab" for easy removal of each single use sheet. Tab 11 that connects the disk shape 10 to the fish tail 12 also has two extensions, for example, the mushroom shaped extensions 13 and 14 providing "attachment tabs" to secure the cover to the stethoscope tubing. The mushroom shaped extensions 13 and 14 each have an application of adhesive on a single side of the oval region, where the adhesive may be applied to mushroom shape 13 on the nearside and on mushroom shape 14 on the far side, such that mushroom shapes 13 and 14 can be raised up and wrapped around the stethoscope hose 203 (see FIG. 2A) and be stuck together. The disk shaped region 10 may also have adhesive on the nearside so that it can be pressed against the flat face 202 of the diaphragm side of the chest piece 201. The disk portion 10 is easily pressed with uniformity across the entire surface 202 of the chest piece 201 to eliminate any voids or air pockets. Any other suitable means may be used to attach the disk 10 portion of base layer 1 to the flat face 202 of the stethoscope, including an electrostatic charge, magnets, etc.

Figure 3:
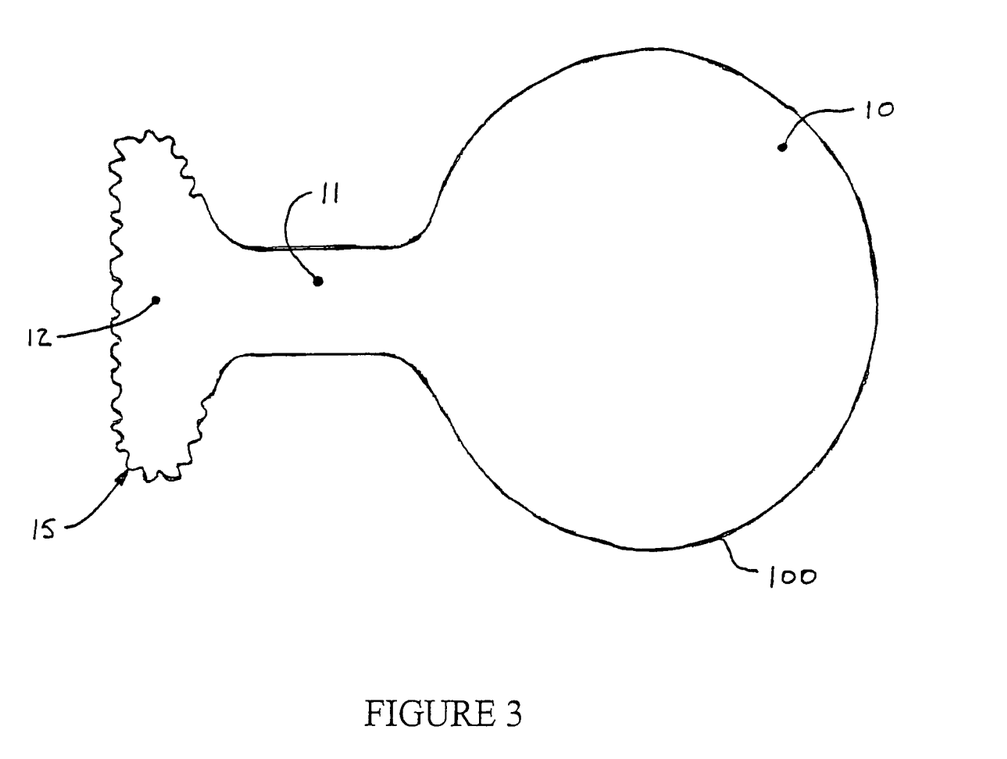
FIG. 3 shows a single protective layer in the flattened condition with the wings not present.

The opposite side of the disk shape 10 away from the stethoscope contains a series of protective layers 100 which, for example, may have the disk shape 10, rectangular tab 11, as well as the fish shape 13, and are thus shown in FIG. 3. The protective layer 100 does not have to follow the mushroom shaped extensions 13 and 14. The cover may utilize a plurality of protective layers 100 and will preferably number between fifteen and twenty. The fish tail 12 region of protective layer 100 may have embossed areas 15, or alternatively be corrugated, or be treated to be anti-cling in nature with other layers 100. This would facilitate easy separation and removal of a used layer. In the region of the disk 10, the protective layers 100 shall cascade 16 so that each successive outer layer overlaps and therefore both encompasses and protects the layer below. Also, in the disk region 10, the protective layers 100 shall be embossed with curvature to resemble the curved region 204 of the chest piece, thus allowing the chest piece to nest within the cover.

As various changes could be made in the above constructions without departing from the scope of the invention, it is intended that all matter contained in the above descriptions shall be interpreted as illustrative and not in a limiting sense. In the views shown it can be seen that several objects of the invention are achieved with differing advantageous results attained.

We claim:

1. A disposable stethoscope cover that covers at least the surface of a diaphragm of a stethoscope chest piece that contacts a patient during use, said cover comprising two or more flexible sheets with each having a top and a bottom surface, wherein said bottom surface of each sheet of said two or more sheets is releasably attached to said top surface of an adjacent sheet except said bottom surface of an innermost sheet of said two or more sheets, said bottom surface of said innermost sheet contacting at least a portion of said stethoscope chest piece, said two or more sheets further comprising a head portion, a body portion, and at least first and second wings laterally extending from said body portion, at least one of said first and second wings having an adhesive on at least one surface thereof for securing said first wing to said second wing when said wings are folded around at least a portion of a tube of said stethoscope.

2. The disposable stethoscope cover according to claim 1 further comprising a tear perforation at said neck, said tear perforation being usable for separating a portion of an outermost sheet from said two or more sheets of said cover.

3. The disposable stethoscope cover according to claim 1 wherein said cover further comprises a breast portion being connected by a neck to said head portion, wherein said breast portion covers said stethoscope diaphragm and said head wraps around said chest piece to cover a bell of said stethoscope; and wherein said breast and said head each further comprise a first and second panel extending laterally therefrom, each of said first and second panels of said head and said breast being usable for securing said cover to said stethoscope chest piece using adhesive.

4. The disposable stethoscope cover according to claim 3 wherein said wings are on said hip portion.

5. The disposable stethoscope cover according to claim 4 wherein said hip portion has a first wing, a second wing and a body between said wings and wherein said adhesive is only on said wings.

6. The disposable stethoscope cover according to claim 5 wherein said second sheet of said two or more sheets is on top of said first sheet, and wherein each succeeding sheet of said two or more sheets is stacked successively thereon and ending with an outer sheet.

7. The disposable stethoscope cover according to claim 2 wherein each of said two or more sheets are releaseably attached to an inner adjacent sheet, and wherein an outermost sheet may be removed and discarded after use, said removal causing said inner sheet adjacent to said outermost sheet to become a new outermost sheet.

8. The disposable stethoscope cover according to claim 7 further comprising a grab area adjacent to said hips for said removal of said outermost sheet.

9. A disposable stethoscope cover that covers at least the surface of a diaphragm of a stethoscope that contacts a patient during use said cover comprising a flexible sheet having a top and a bottom surface said sheet having an adhesive material on a portion of the surface thereof that secures said sheet to said surface of said diaphragm said sheet further comprising an orifice extending from said top surface to said bottom surface said orifice adapted to receive a portion of a tube section of said stethoscope, and at least one wing extending from said sheet said wing having an adhesive on at least one surface thereof for securing said wing to said sheet when said wing is folded over at least a portion of a tube of said stethoscope.

10. The disposable stethoscope cover according to claim 9 wherein there is a tear perforation separating an area of said sheet where said orifice is located and the area of said sheet that adheres to said diaphragm.

11. The disposable stethoscope cover according to claim 10 wherein said sheet has a head portion where said orifice is located, a neck portion, a shoulder portion, a breast portion, a waist portion and a hip portion.

12. The disposable stethoscope cover according to claim 11 wherein there are first and second wings.

13. The disposable stethoscope cover according to claim 12 wherein said wings are on said hip portion.

14. The disposable stethoscope cover according to claim 13 wherein said hip portion has a first wing, a second wing and a body between said wings and wherein said adhesive is only on said wings.

15. The disposable stethoscope cover according to claim 14 further comprising grab area adjacent said hips for pulling a portion of said sheet away from the diaphragm.

16. A disposable cover for use in protecting at least a portion of a stethoscope chest piece, said cover comprising: a plurality of flexible sheets wherein a first inner sheet has succeeding sheets stacked and releasably attached thereon until a last sheet forms an outer sheet of said plurality of sheets; each of said plurality of sheets comprising a body, said body having an upper end, a lower end, a first side and a second side, a portion of said first and second sides being formed to wrap around and releasably attach to each other using adhesive on at least one of said first or second sides; a grab area, said grab area extending from said body upper end for successively peeling said outer sheet; and a diaphragm cover portion and a bell cover portion, said diaphragm cover portion extending from said lower end of said body with said bell cover portion being connected by a neck area to said diaphragm cover portion, each of said diaphragm portion and said bell portion having two wings extending laterally, and wherein when said bell cover portion is wrapped around to be approximately parallel to said diaphragm portion, said disposable cover being releasably secured thereto by said wings of said bell portion releasably attaching to said wings of said diaphragm portion using adhesive on at least one of said of wings of said diaphragm portion or said bell portion; said outer sheet being usable and peelable to expose a new hygienic outer layer of said plurality of layers.

17. The disposable cover according to claim 16 wherein said body portion is wrapped around and secured about tubing of a stethoscope, and wherein said diaphragm cover portion is releasably attached to a stethoscope diaphragm using adhesive.

18. The disposable cover according to claim 17 wherein said bell cover portion is releasably attached to a stethoscope bell using adhesive.

19. The disposable cover according to claim 18 wherein said bell cover portion comprises a hole, said hole permitting unimpeded sound transmission.

20. A disposable cover for use in protecting a diaphragm and a bell of a stethoscope chest piece, said cover comprising: a plurality of flexible sheets wherein a first inner sheet has succeeding sheets stacked and releasably attached thereon until a last sheet forms an outer sheet of said plurality of sheets; each of said plurality of sheets comprising a body, a diaphragm cover portion, and a bell cover portion; said body having an upper end, a lower end, a first side and a second side, a portion of said first and second sides being formed to wrap around and be slidable with respect to a portion of a tube of said stethoscope and releasably attach to each other using adhesive on at least one of said first or second sides; said diaphragm cover portion extending from said lower end of said body with said bell cover portion being connected by a neck area to said diaphragm cover portion, each of said diaphragm portion and said bell portion having two wings extending laterally; and wherein after said body portion is wrapped around and slidably secured about said tubing of said stethoscope, said bell cover portion is wrapped around a chest piece to cover a bell of said stethoscope, with said diaphragm cover portion covering said diaphragm of said stethoscope; said disposable cover being releasably secured to said chest piece; said outer sheet being usable and peelable thereafter to expose a new hygienic outer layer of said plurality of layers.

21. The disposable cover according to claim 20 wherein said bell cover portion comprises a hole, said hole permitting unimpeded sound transmission.

22. The disposable cover according to claim 21 further comprising a tear perforation in said neck area of each of said plurality of flexible sheets, said tear perforation assisting said peeling.

23. The disposable cover according to claim 22, wherein said tear perforation permits peeling to expose a new hygienic outer layer for only said diaphragm cover portion of said plurality of layers.

24. The disposable cover according to claim 22, wherein said tear perforation permits peeling to expose a new hygienic outer layer for only said bell cover portion of said plurality of layers.

25. The disposable cover according to claim 22, wherein said disposable cover is releasably secured to said chest piece by said wings of said bell cover portion releasably attaching to said wings of said diaphragm cover portion using adhesive on at least one of said of wings of said diaphragm portion and/or said bell portion.

26. The disposable cover according to claim 22, wherein said disposable cover is releasably secured to said chest piece by said wings of said bell cover portion releasably attaching to a side wall of said chest piece using adhesive.

27. The disposable cover according to claim 22, wherein said disposable cover is releasably secured to said chest piece by adhesive releasably securing said bell cover portion to said stethoscope bell.

28. The disposable cover according to claim 22, wherein said disposable cover is releasably secured to said chest piece by said bell cover portion releasably attaching to said chest piece bell using adhesive, and by said wings of said diaphragm cover portion releasably attaching to a side wall of said chest piece using adhesive.

29. The disposable cover according to claim 22, wherein said disposable cover is releasably secured to said chest piece by said bell cover portion releasably attaching to said chest piece bell using adhesive, and by said diaphragm cover portion releasably attaching to said chest piece diaphragm using adhesive.

30. The disposable cover according to claim 22, wherein said disposable cover is releasably secured to said chest piece by said wings of said bell cover portion releasably attaching to a side wall of said chest piece using adhesive, and by said wings of said diaphragm cover portion releasably attaching to a side wall of said chest piece using adhesive.

31. The disposable cover according to claim 22, wherein said disposable cover is releasably secured to said chest piece by said wings of said bell cover portion releasably attaching to a side wall of said chest piece using adhesive, and by said diaphragm cover portion releasably attaching to said chest piece diaphragm using adhesive.

32. The disposable cover according to claim 22, wherein said disposable cover is releasably secured to said chest piece by said bell cover portion releasably attaching to said chest piece bell using adhesive, by said diaphragm cover portion releasably attaching to said chest piece diaphragm using adhesive, and by said wings of said bell cover portion releasably attaching to said wings of said diaphragm cover portion using adhesive on at least one of said of wings of said diaphragm portion or said bell portion.

* * * * *